United States Patent [19]

Perry et al.

[11] Patent Number: 5,531,786
[45] Date of Patent: * Jul. 2, 1996

[54] MEDICAL PROTHESES CONTAINING A GEL-FILLER COMPRISING PRINCIPALLY WATER AND CELLULOSE DERIVATIVE

[76] Inventors: Larry C. Perry, 3333 Country Ridge Dr., Antioch, Tenn. 37013; G. Patrick Maxwell, 4416 Gerald Pl., Nashville, Tenn. 37205

[*] Notice: The portion of the term of this patent subsequent to Apr. 13, 2012, has been disclaimed.

[21] Appl. No.: 188,107

[22] Filed: Jan. 28, 1994

Related U.S. Application Data

[63] Continuation-in-part of Ser. No. 867,417, Apr. 13, 1992, Pat. No. 5,282,857.

[51] Int. Cl.$^6$ ........................................................ A61F 2/12
[52] U.S. Cl. ........................................................... 623/8
[58] Field of Search ............................ 623/8, 11; 424/422, 424/423

[56] References Cited

U.S. PATENT DOCUMENTS

| | | | |
|---|---|---|---|
| 4,292,300 | 9/1981 | Byrne et al. | 424/19 |
| 4,455,143 | 6/1984 | Theeuwes et al. | 604/890 |
| 4,563,182 | 1/1986 | Stoy et al. | 604/285 |
| 4,601,893 | 7/1986 | Cardinal | 424/15 |
| 4,605,691 | 8/1986 | Balazs et al. | 524/27 |
| 4,731,081 | 3/1988 | Tiffany et al. | 623/8 |
| 4,743,248 | 5/1988 | Bartoo et al. | 604/892.1 |
| 4,772,284 | 9/1988 | Jefferies et al. | 623/8 |
| 4,778,465 | 10/1988 | Wilkins | 623/8 |
| 4,781,714 | 11/1988 | Eckenhoff et al. | 604/890.1 |
| 4,787,905 | 11/1988 | Loi | 623/7 |
| 4,790,848 | 12/1988 | Cronin | 623/8 |
| 4,819,617 | 4/1989 | Goldberg et al. | 128/897 |
| 4,904,260 | 2/1990 | Ray et al. | 623/17 |
| 4,955,881 | 9/1990 | Eckenhoff | 604/890.1 |
| 4,957,494 | 9/1990 | Wong et al. | 604/892.1 |
| 4,995,882 | 2/1991 | Destouet et al. | 623/8 |
| 5,008,102 | 4/1991 | York | 424/59 |
| 5,035,891 | 7/1991 | Runkel et al. | 424/423 |
| 5,067,965 | 11/1991 | Ersek et al. | 623/66 |
| 5,116,370 | 5/1992 | Foglietti | 623/8 |
| 5,116,371 | 5/1992 | Christensen et al. | 623/11 |
| 5,123,923 | 6/1992 | Pommier et al. | 623/16 |
| 5,192,326 | 3/1993 | Bao et al. | 623/17 |
| 5,208,032 | 5/1993 | Scanes et al. | 424/422 |
| 5,282,857 | 2/1994 | Perry et al. | 623/8 |
| 5,344,451 | 9/1994 | Dayton | 623/8 |

FOREIGN PATENT DOCUMENTS

| 8906918 | of 1989 | South Africa. |
| 929093 | 5/1982 | U.S.S.R.. |

OTHER PUBLICATIONS

Carter-Wallace, Inc., H-R Lubricating Jelly Product Sheet.
E. Fougera & Co., Surgilube Product Sheet.
Radiolucent Prosthetic Gel, From the Department of Pediatrics at the University of Minnesota Hospitals, Department of Radiology at the Minneapolis Veterans Medical Center, Jul. 1990, pp. 885–891.
International Application WO90/04971, May 17, 1990.
European Search Report EP 93 30 2664.
Database WPI, Derwent Publications Ltd., London, GB; AN 90–305251.
Database WPI, Derwent Publications Ltd., London, GB; AN 83–31383K.

*Primary Examiner*—Michael J. Milano
*Attorney, Agent, or Firm*—Renner, Otto, Boiselle & Sklar

[57] ABSTRACT

This invention relates to a medical prosthesis containing a gel filler material comprising principally a cellulose derivative in water. The gel filler in the prosthesis may further contain a lubricating agent. The invention also relates to a method of augmenting or reconstructing a human breast comprising the steps of subcutaneously implanting a medical prosthesis with the gel filler material into a human body. In another aspect, the invention relates to a method of preparing medical protheses comprising the steps of filling an outer envelope of a medical-grade elastomer with the gel filler material and sealing the envelope to form a medical prosthesis. The components of the gel are preferably biocompatible so as not adversely to affect human beings. The materials used to make the gel filler are non-toxic. The prostheses of the present invention have similar characteristics to the human breast. These protheses may be used for breast augmentation or reconstruction.

22 Claims, No Drawings

5,531,786

MEDICAL PROTHESES CONTAINING A GEL-FILLER COMPRISING PRINCIPALLY WATER AND CELLULOSE DERIVATIVE

CROSS REFERENCE TO RELATED APPLICATION

This application is a continuation-in-part of U.S. Ser. No. 07/867,417, filed Apr. 13, 1992, now U.S. Pat. No. 5,282,857.

TECHNICAL FIELD OF THE INVENTION

This invention relates to medical prostheses, especially those used for a breast or a testicular prosthesis.

BACKGROUND OF THE INVENTION

The reconstruction or cosmetic variation of a breast, such as often performed following mastectomy, has become an increasingly frequent surgical procedure. The development and use of silicone-gel and silicon-filled implants have contributed to the popularity of this procedure. Recent concern over the effects of the filler of these implants, e.g. silicone-gel, on the health of women has lead to a decrease in their use.

Saline has been suggested as a filler for breast implants. Saline is considered biocompatible. However, when used in breast implant, saline does not provide the density or feel of natural breast tissue.

Therefore, it is desirable to provide a filler material for an implant which simulates or duplicates the characteristics of a natural breast. Further, it is desirable to provide a material that does not have an adverse effect on the human body containing the implants.

WO 90/04971, with Pennel et al. as inventors and corresponding to U.S. Pat. No. 4,983,585, relates to improved viscoelastic fluids or gels for use in surgery and other therapies. The viscoelastic fluid or gel has as its principal ingredients polyethyleneoxide in a physiological balanced salt solution. The viscoelastic fluids or gels may include a viscosity enhancer or stabilizer. The viscosity enhancers or stabilizers include hydroxypropyl methylcellulose, carboxymethyl cellulose, hydroxypropyl cellulose, hydroxyethyl cellulose, methyl cellulose or mixtures thereof, polyvinyl pyrrolidone, or polyvinyl alcohol. Polyethyleneoxide is an essential ingredient in the viscoelastic fluids or gels. Pennel et al. contains no suggestion that useful fluids or gels may be prepared without polyethyleneoxide.

U.S. Pat. No. 4,772,284 relates to a breast prosthesis with improved bio-compatibility and methods of making the same. The breast implant is a single lumen implantable and biocompatible breast implant composed of an outer membrane of silastic, medical grade silicone, and an inner material selected from the group consisting of purified reconstructive collagen gel and a purified gel of poly-alpha amino homopolymers or random copolymers having a molecular weight of from 5,000 to 400,000.

U.S. Pat. No. 4,787,905 relates to gel for breast prostheses. The gel is a mixture of hydroxy-terminated polybutadiene resin, diundecylphthalate, polymethylenepolyphenyl isocyanate, and dibutyltin dilaurate catalyst, wherein the mixture is cured to form the gel.

U.S. Pat. No. 4,790,848 relates to a breast implant with multiple lumens. The implant comprises an inner lumen of substantially spherical shape. The inner lumen is unattached, or free-floating. The lumens are filled with silicone gel or similar fluid material.

U.S. Pat. No. 4,995,882 relates to a radiolucent breast implant. The radiolucent breast implant is composed of a silicone envelope filled with any biocompatible triglyceride such as peanut oil or sunflower oil or any other material having an effective atomic number of 5.9, which is the effective atomic number of fat. This breast implant is radiolucent in that it duplicates the photo-electric interference of fat which is the major effect producing subject at low radiation levels as used in mammography.

SUMMARY OF THE INVENTION

This invention relates to a medical prostheses containing a gel filler material comprising principally a cellulose derivative in water. The gel filler in the prostheses may further contain a lubricating agent. The invention also relates to a method of augmenting or reconstructing a human breast comprising the steps of subcutaneously implanting a medical prosthesis with the gel filler material into a human body. In another aspect, the invention relates to a method of preparing medical protheses comprising the steps of filling an outer envelope of a medical-grade elastomer with the gel filler material and sealing the envelope to form a medical prosthesis. The components of the gel are preferably biocompatible so as not adversely to affect human beings. The materials used to make the gel filler are non-toxic. Prosthesis containing the lubricating agent have a decreased tendency of failure caused by internal friction on the envelope. The prostheses of the present invention have similar characteristics to the human breast. These prostheses may be used for breast augmentation or reconstruction.

DETAILED DESCRIPTION OF THE INVENTION

As used in the specification and appended claims, the use of the term "gel" refers to gelatinous and "jelly-like" materials which provide the physical characteristics of the medical prosthesis of the present invention. The gel filler is composed principally of a cellulose derivative and water. The use of the term principally does not preclude other additives from the gel filler which add additional properties to the filler material.

The prosthesis of the present invention may be used as an implant anywhere in the human body, especially as replacements for breasts and testicles. These prostheses are also useful for augmentation of the breasts. It should be recognized that the characteristics of the prosthesis may be altered by altering the density of the gel of the prosthesis. In one embodiment, the density of the gel of the prosthesis approximates that of the human breast. The gel of the prosthesis generally has a density in $g/cm^3$ from about 0.8 up to about 1.5, or from about 0.9 up to about 1.4, or from about 0.95 up to about 1.3, or up to about 1.2. Here, as well as elsewhere in the specification, the range and ratio limits may be combined. The density of the gel is determined by the amount of cellulose derivative used in the filler material. The density of the filler material is maintained and does not change when the implant is used.

In one embodiment, the gel is free of one or more of the following hyaluronic acid or its derivatives, polyethyleneoxide, polyvinylpyrrolidone, polyvinyl alcohol, polymers containing esters of acrylic or methacrylic acids, polyacrylonitrile.

The prosthesis is comprised of an outer envelope. The envelope is generally a medical-grade elastomeric material. An example of a particularly useful envelope is a silicone envelope. The outer envelope is filled and sealed.

The filler material of the prosthesis comprises a gel formed principally from water and a cellulose thickening agent. The water is generally present in a major amount, usually an amount greater than 70%, or greater than about 75%, or greater than about 80% by weight of the gel. In one embodiment, the water is present in an amount from about 80% up to about 95%, or from about 85% up to about 93% by weight of the gel. The water is preferably purified and sterile as is known to those in the art. In one embodiment, the water is saline.

The cellulose derivative provides thickening of the water to form the gel of the present invention. As is known, cellulose is a polymer of glucose rings derived from plants. In one embodiment, the cellulose derivative is a cellulose ether. Examples of cellulose thickening agents include alkylcelluloses, such as methylcellulose and ethylcellulose; hydroxyalkylcelluloses, such as hydroxyethylcellulose and hydroxypropylcellulose; hydroxyalkyl alkylcelluloses, such as hydroxyethyl methylcellulose, hydroxypropyl methylcellulose, and hydroxyethyl ethylcellulose; metal carboxyalkylcelluloses, such as potassium, lithium, magnesium, calcium, or sodium carboxymethylcellulose; metal carboxyalkyl hydroxyalkylcelluloses, such as potassium, lithium, magnesium or sodium carboxymethyl hydroxyethylcellulose; and mixtures of two or more thereof. Preferably, the cellulose thickening agent is hydroxyethylcellulose or methylcellulose.

As known to those skilled in the art, the cellulose thickening agent or agents may also be cross-linked by any conventional means in order to maintain biostability of these products.

The cellulose thickening agent is present in an amount sufficient to gel the water. In one embodiment, the cellulose thickening agent is present in an amount to produce a density which approximates the density of the human breast. The cellulose thickening agent is generally present in an amount from about 0.5% up to about 15%, or from about 1% up to about 10%, or up to about 8% by weight of the gel filler.

In one embodiment, the gel filler further comprises a lubricating agent. The lubricating agent can be any agent which reduces the internal friction in the envelope. Prostheses containing the lubricating agent have a decreased tendency of failure caused by internal friction on the envelope. The lubricating agent may be a polyol. Examples of useful polyols include ethyleneglycol, propyleneglycol, butanetriol, butanediol, hexanediol, hexanetriol and the like. Preferably, the lubricating agent is glycerol or propyleneglycol. In another embodiment, the lubricating agent may be any glyceride, preferably a triglyceride. Examples of glyceride lubricants include coconut triglycerides, and oleyltriglycerides.

In addition to the water, cellulose thickening agents and optionally lubricating agents, the gel filler may additionally contain other additives which act as preservatives, antioxidants, pH controlling agents and antibacterial agents in the gel. Examples of these agents include methylparaben, propylparaben, sodium hydroxide, glucono delta lactate, chlorhexidine gluconate, propyleneoxide and the like.

In one embodiment, the prosthesis of the present invention may be commercially available surgical and personal lubricant gels. Examples of these gels include Surgilube® surgical lubricant available commercially from E. Fougera & Company, HR® Lubricating Jelly available commercially from Carter-Wallace, Inc. and K-Y Lubricating Jelly available commercially from Johnson & Johnson.

As described above the prosthesis of the present invention may be used as replacements for body tissues or augmentation of body tissues. In one embodiment, the protheses are used for breast reconstruction and/or augmentation. The process for using the prosthesis involves placing the prosthesis of the present invention subcutaneously in a human being in a region where replacement and/or augmentation is desired. For instance, for breast augmentation, the implant is subcutaneously placed into the breast region. The process for placing the implant into a human is known to those skilled in the art and generally involved inserting the implant through an incision in the chest. Methods of placing protheses is known to those in the art.

The invention further comprises the process of preparing medical prostheses which involves the steps of filling an outer envelope of a medical grade elastomer with a gel as described herein. The envelope is sealed to form the medical prosthesis. The sealing procedure of the envelopes is known to those skilled in the art.

In another embodiment, a medical prosthesis is prepared by adding a cellulose thickening agent to an outer envelope of a medical grade elastomer. Water, usually saline, is added to the envelope and the gel is formed in the envelope.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A sealed implantable prosthesis for implantation into soft tissue for replacing or augmenting the tissues, comprising an outer envelope forming a hollow sealed shell defining an enclosed volume, the hollow shell being made from a biocompatible medical-grade elastomer suitable for implantation into a human body and being filled with a gel filler with a predetermined density to provide a feel simulating the characteristic of the corresponding tissue part, wherein the gel filler of said predetermined density is obtained from a colloidal mixture of water and a cellulose derivative selected from the group consisting of an alkylcellulose, a hydroxyalkylcellulose, a hydroxyalkyl alkylcellulose, a metal carboxyalkylcellulose, a metal carboxyalkyl hydroxyalkylcellulose, a cross-linked cellulose derivative, and mixtures of two or more thereof, provided that the gel filler is free of polyethyleneoxide, wherein the gel filler is retained in the sealed shell to maintain constant its determined density.

2. The implantable prosthesis of claim 1 wherein the cellulose derivative is selected from the group consisting of hydroxyethyl methylcellulose; hydroxypropyl methylcellulose; potassium, lithium, magnesium or calcium carboxymethylcellulose; potassium, lithium, or magnesium carboxymethyl, hydroxyethylcellulose; or mixtures of two or more thereof.

3. The implantable prosthesis of claim 1 wherein the cellulose derivative is selected from the group consisting of methylcellulose and hydroxyethylcellulose.

4. The implantable prosthesis of claim 1 wherein the envelope is a medical-grade silicon.

5. The implantable prosthesis of claim 1 further comprising a lubricating agent.

6. The implantable prosthesis according to claim 1, wherein the water is present in the gel filler in an amount greater than about 70% by weight of the gel filler.

7. The implantable prosthesis according to claim 6, wherein the water is present in an amount from about 75% to about 95% by weight of the gel filler.

8. The implantable prosthesis according to claim 6, wherein the cellulose derivative is present in an amount of about 0.5% to about 15% by weight of the gel filler.

9. The implantable prosthesis according to claim 1, wherein the water is present in the gel filler in a major amount so that the volume of the gel filler is determined substantially by the volume of the water.

10. The implantable prosthesis according to claim 1, wherein the gel filler consists essentially of a mixture of water and the cellulose derivative.

11. The implantable prosthesis according to claim 6, wherein the cellulose derivative is present in an amount from about 0.5% to about 8% by weight of gel filler.

12. The implantable prosthesis according to claim 1, wherein the gel filler has a density from about 0.8 to about 1.5 g/cm$_3$.

13. A sealed implantable prosthesis for implantation into soft tissue for replacing or augmenting the tissues, comprising an outer envelope forming a hollow sealed shell defining an enclosed volume, the hollow shell being made from a biocompatible medical-grade elastomer suitable for implantation into a human body and being filled with a gel filler with a predetermined density to provide a feel simulating the characteristic of the corresponding tissue part, wherein the gel filler of said predetermined density is obtained from a colloidal mixture of water and a cellulose derivative selected from the group consisting of hydroxyethyl methylcellulose; hydroxypropyl methylcellulose; potassium, lithium, magnesium or calcium carboxymethylcellulose; potassium, lithium, or magnesium carboxymethyl hydroxyethylcellulose; and mixtures of two or more thereof, provided that the gel filler is free of polyethyleneoxide, wherein the gel filler is retained in the sealed shell to maintain constant its determined density.

14. The implantable prosthesis of claim 13 wherein the envelope is a medical-grade silicone.

15. A sealed implantable prosthesis according to claim 13, wherein the cellulose derivative in said gel filler includes a cross-linked cellulose derivative.

16. A sealed implantable prosthesis for implantation into soft tissue for replacing or augmenting the tissues, comprising an outer envelope forming a hollow sealed shell defining an enclosed volume, the hollow shell being made from a biocompatible medical-grade elastomer suitable for implantation into a human body and being filled with a gel filler with a predetermined density to provide a feel simulating the characteristic of the corresponding tissue part, wherein the gel filler of said predetermined density is obtained from a colloidal mixture of water and an alkylcellulose or a hydroxyalkyl alkylcellulose, and mixtures thereof, provided that the gel filler is free of polyethyleneoxide, wherein the gel filler is retained in the sealed shell to maintain constant its determined density.

17. The implantable prosthesis of claim 16 wherein the alkyl cellulose is methylcellulose.

18. The implantable prosthesis of claim 16 wherein the hydroxyalkylcellulose is hydroxyethylcellulose.

19. A method of augmenting or reconstructing a human breast, comprising the step of subcutaneously implanting the sealed medical prosthesis of claim 1 into a human being.

20. A sealed implantable prosthesis for implantation into soft tissue for replacing or augmenting the tissues, comprising an outer envelope forming a hollow sealed shell defining an enclosed volume, the hollow shell being made from a biocompatible medical-grade elastomer suitable for implantation into a human body and being filled with a gel filler with a predetermined density to provide a feel simulating the characteristic of the corresponding tissue part, wherein the gel filler of said predetermined density is obtained from a colloidal mixture of water and a cellulose derivative selected from the group consisting of an alkylcellulose, a hydroxyalkylcellulose, a hydroxyalkyl alkylcellulose, a metal carboxyalkylcellulose, a metal carboxyalkyl hydroxyalkylcellulose and mixtures of two or more thereof, provided that the gel filler is free of polyethyleneoxide, wherein the gel filler is retained in the sealed shell to maintain constant its determined density.

21. A sealed implantable prosthesis according to claim 20, wherein the cellulose derivative in said gel filler includes a cross-linked cellulose derivative.

22. A sealed implantable prosthesis for implantation into soft tissue for replacing or augmenting the tissues, comprising an outer envelope forming a hollow sealed shell defining an enclosed volume, the hollow shell being made from a biocompatible medical-grade elastomer suitable for implantation into a human body and being filled with a gel filler with a predetermined density to provide a feel simulating the characteristic of the corresponding tissue part, wherein the gel filler of said predetermined density is obtained from a colloidal mixture of water and a biocompatible cellulose derivative, a cross-linked cellulose derivative, and mixtures of two or more thereof, said biocompatible cellulose, respectively, cross-linked cellulose derivative(s) being capable of producing said biocompatible gel of predetermined density by the amount thereof admixed to water present in the mixture in a major amount, provided that the gel filler is free of polyethyleneoxide, wherein the gel filler is retained in the sealed shell to maintain constant its predetermined density.

* * * * *